United States Patent [19]
Prevost et al.

[11] Patent Number: 5,455,176
[45] Date of Patent: Oct. 3, 1995

[54] MICROBIAL CONTAMINATION TEST DEVICE

[75] Inventors: André Prevost; Jean Barbeau, both of Montréal; Ludger Cote, Matane; Robert Charland, Boucherville, all of Canada

[73] Assignee: University de Montreal, Montreal, Canada

[21] Appl. No.: 212,256

[22] Filed: Mar. 14, 1994

[51] Int. Cl.$^6$ .............................. C12M 1/24; C12M 1/34; C12Q 1/04; C12Q 1/06
[52] U.S. Cl. .................. 435/287.4; 435/34; 435/39; 435/296; 435/808; 435/287.1
[58] Field of Search .................. 435/296, 286, 435/808, 291, 39, 34

[56] References Cited

U.S. PATENT DOCUMENTS

| | | | |
|---|---|---|---|
| 3,083,145 | 3/1963 | Ryan | 435/296 |
| 3,621,016 | 11/1971 | Berger | 435/36 |
| 3,657,073 | 4/1972 | Burton et al. | 435/291 |
| 3,718,543 | 2/1973 | Lagomarsino | 435/37 |
| 3,875,012 | 4/1975 | Dorn et al. | 435/39 |
| 4,263,405 | 4/1981 | Melnick et al. | 435/291 |
| 4,385,115 | 5/1983 | de Zabala et al | 435/32 |
| 4,434,235 | 2/1984 | Rabi et al. | 436/110 |
| 4,565,783 | 1/1986 | Hansen et al. | 435/299 |
| 4,639,419 | 1/1987 | Olson et al. | 435/5 |
| 4,693,968 | 9/1987 | Kitakawa | 435/7 |
| 4,698,308 | 10/1987 | Ikeda | 435/291 |
| 4,904,605 | 2/1990 | O'Brien et al. | 436/169 |
| 5,081,017 | 1/1992 | Longoria | 435/30 |
| 5,132,085 | 7/1992 | Pelanek | 422/55 |
| 5,188,946 | 2/1993 | Ward et al. | 435/91 |
| 5,232,838 | 8/1993 | Nelson et al. | 435/30 |
| 5,248,595 | 9/1993 | Boyer et al. | 435/7.32 |
| 5,270,174 | 12/1993 | Rosenberg | 435/34 |

FOREIGN PATENT DOCUMENTS

| | | |
|---|---|---|
| 0174195 | 3/1986 | European Pat. Off. . |
| 0233048 | 8/1987 | European Pat. Off. . |
| 0537826 | 4/1993 | European Pat. Off. . |
| 0119992 | 9/1979 | Japan . |
| 0021565 | 2/1993 | Japan . |

*Primary Examiner*—Jeffrey E. Russel
*Attorney, Agent, or Firm*—Merchant, Gould, Smith, Edell, Welter & Schmidt

[57] ABSTRACT

A test device for evaluating microbial contamination of a liquid comprises a hollow container unit defining a first compartment for containing a nutrient for growing microorganisms and a second compartment for containing a contamination indicating coloring agent. The first compartment is filled with the liquid to be tested, which liquid mixes with the nutrient to grow the microorganisms during a predetermined period of time. During growth of the microorganisms, a sealing mechanism isolates the first and second compartments from each other. After the predetermined period of time has elapsed, the sealing mechanism is operated to establish communication between the first and second compartments to thereby mix the coloring agent from the second compartment with the liquid from the first compartment. In the presence of microorganisms, the coloring agent colors the liquid to indicate contamination thereof.

9 Claims, 2 Drawing Sheets

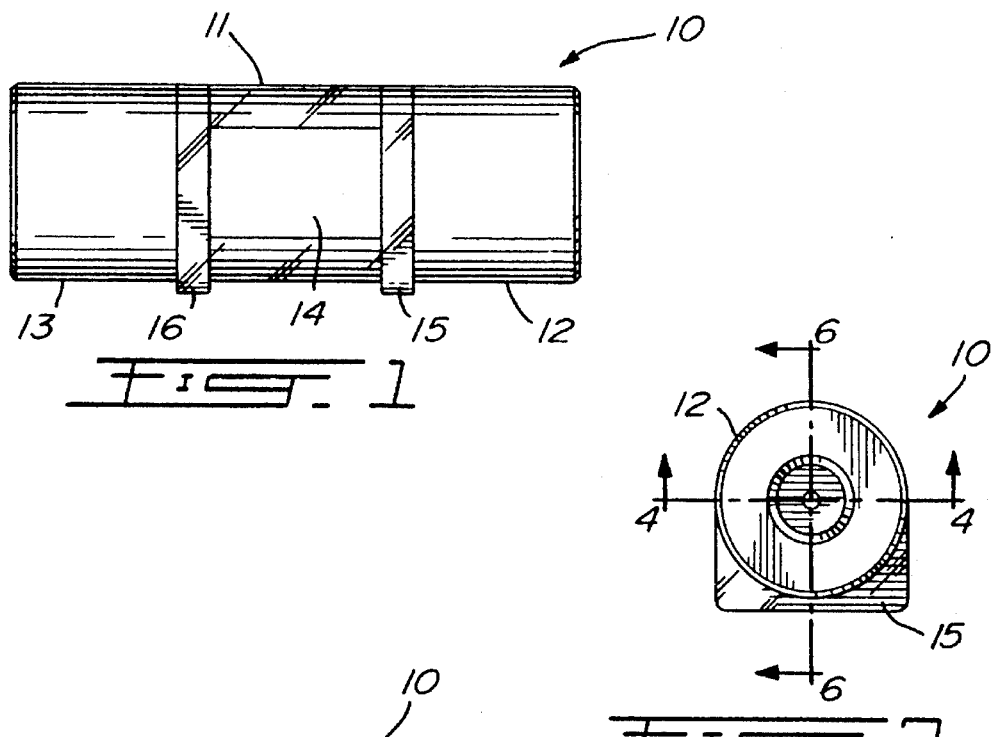
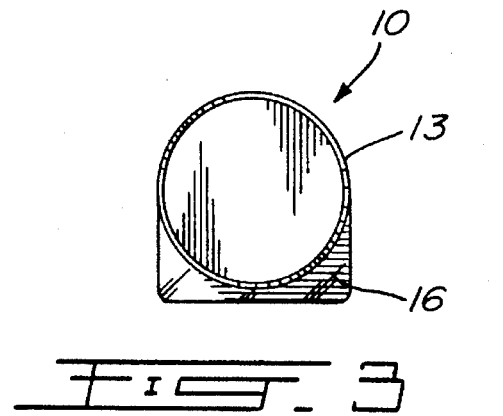
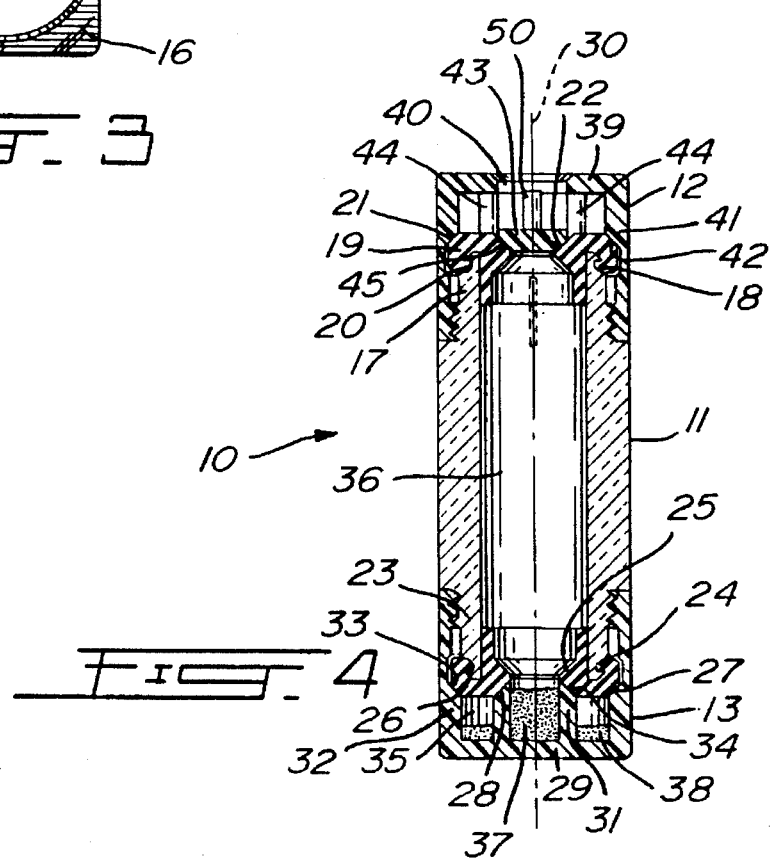

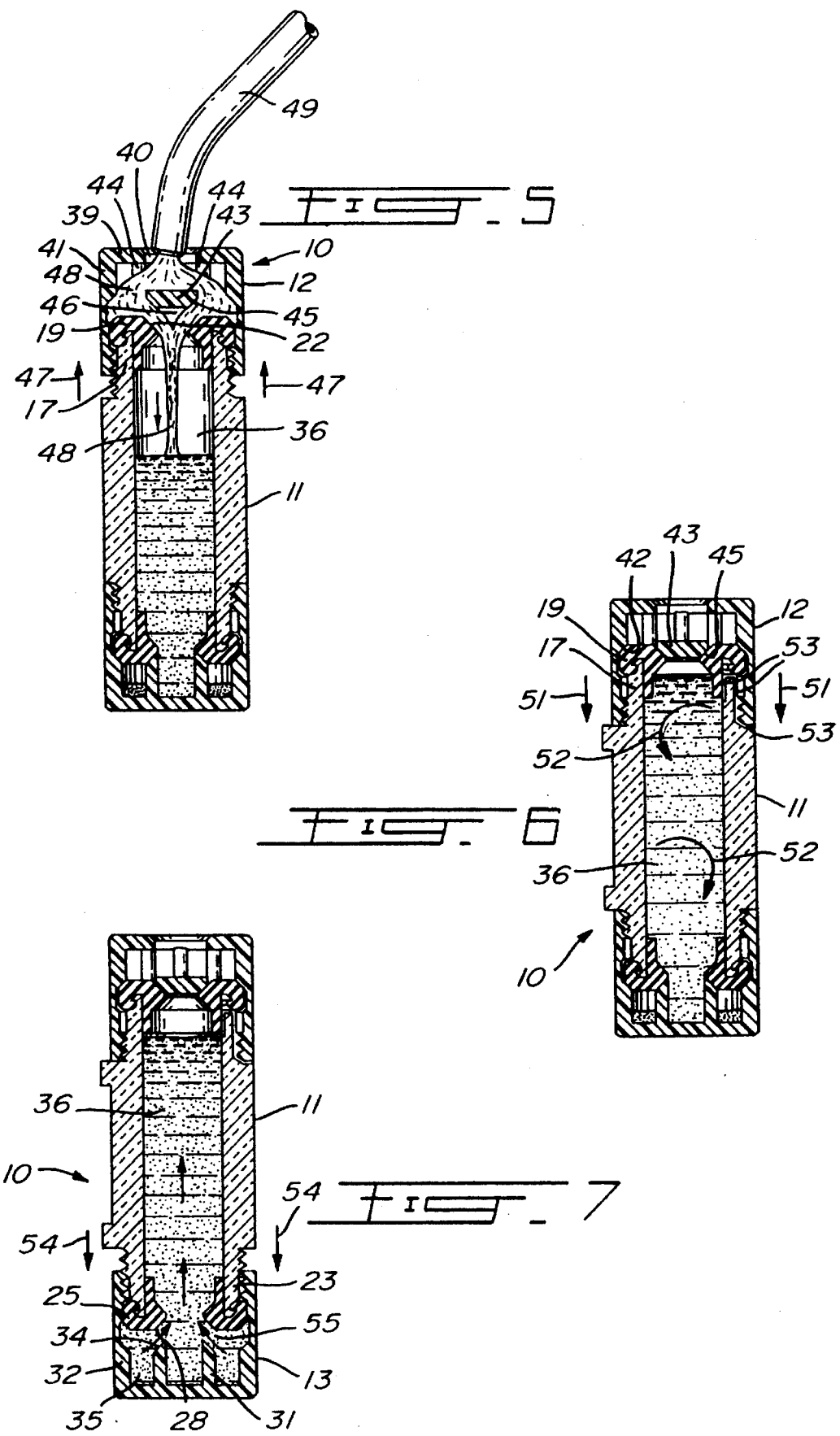

MICROBIAL CONTAMINATION TEST DEVICE

BACKGROUND OF THE INVENTION

1. Field of the invention:

The present invention relates to a test device for evaluating microbial contamination of a liquid, in particular but not exclusively bacterial contamination of water supplied through a tubing system such as the water lines of a dental unit.

2. Brief description of the prior art:

Many microbial contamination test devices have been proposed in the prior art. Examples are given in the following United States patents:

| 4,263,405 | (Melnick et al.) | 1981 |
| 4,639,419 | (Olson et al.) | 1987 |
| 5,081,017 | (Longoria) | 1992 |

In many instances, microbial testing requires growth of the microorganisms of the liquid under test before adding the contamination indicating agent which colors the liquid in the presence of microorganisms. The above prior art test devices are not well suited for carrying out these two steps sequentially.

OBJECT OF THE INVENTION

A first object of the present invention is therefore to overcome the above mentioned drawback of the prior art microbial contamination test devices.

A second object of the invention is to provide a microbial contamination test device containing, in a first compartment, a nutrient for growing the microorganisms of the liquid under test and, in a second compartment connectable to the first compartment, a contamination indicating agent to be mixed with the liquid after the microorganism growing step has been completed.

SUMMARY OF THE INVENTION

More specifically, in accordance with the present invention, there is provided a test device for evaluating microbial contamination of a liquid, comprising a hollow container unit defining a first compartment for containing a nutrient for growing microorganisms and a second compartment for containing a contamination indicating agent, inlet means for introducing the liquid in the first compartment whereby this liquid mixes with said nutrient to grow microorganisms present therein, and sealing means interposed between the first and second compartments and operable (a) to isolate the first and second compartments from each other, or (b) to establish communication between these first and second compartments to mix the agent from the second compartment with the liquid from the first compartment and enable that agent to indicate, in the presence of microorganisms, contamination of the liquid.

Therefore, liquid to be tested can be introduced in the first compartment while the sealing means isolates the first and second compartments from each other. This will enable, in a first step, the nutrient to grow the microorganisms of the liquid. After a certain period of time, the sealing means can be operated to establish communication between the first and second compartments and allow the contamination indicating agent to react to the presence of microorganisms and indicate contamination of the liquid.

Preferably, the nutrient is a lyophilised culture, and the contamination indicating agent is a coloring agent which colors the liquid in the presence of microorganisms.

In accordance with a preferred embodiment of the test device of the invention, the hollow container unit comprises a tubular section and a cap section mounted on one end of the tubular section, the tubular section defining the first compartment and the cap section defining the second compartment. The above mentioned end of the tubular section is substantially cylindrical and externally threaded, and the cap section is formed with a distal end wall and with coaxial inner and outer substantially cylindrical walls connected to and extending from one side of the distal end wall, the second compartment being defined between these inner and outer cylindrical walls and the outer cylindrical wall of the cap section being internally threaded to engage the externally threaded end of the tubular section and enable screwing of the cap section on the tubular section. The inner cylindrical wall of the cap section comprises an annular free end, and the sealing means comprise the inner cylindrical wall and an annular sealing member interposed between the annular free end and the externally threaded end of the tubular section. Accordingly, in operation, the cap section is screwed on the externally threaded end of the tubular section to press the annular sealing member between the annular free end and the externally threaded end and thereby isolate the first and second compartments from each other, and unscrewed to form an annular passage between the annular free end and the externally threaded end whereby the first and second compartments are in communication with each other.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 1 is a side elevational view of the test device according to the invention, comprising a first compartment for containing a nutrient for growing microorganisms and a second compartment for containing a contamination indicating agent;

FIG. 2 is a first end view of the test device of FIG. 1;

FIG. 3 is a second end view of the test device of FIGS. 1 and 2;

FIG. 4 is a cross sectional, top plan view of the test device of FIGS. 1–3, taken along line 4—4 of FIG. 2 and in which the first and second compartments are sealed and isolated from each other;

FIG. 5 is a cross sectional, top plan view of the test device of FIGS. 1–3, taken along line 4—4 of FIG. 2 and showing introduction of liquid in the first compartment;

FIG. 6 is a cross sectional, elevational side view of the test device of FIGS. 1–3, taken along line 6—6 of FIG. 2 and in which the first compartment is filled with liquid mixed with the nutrient for growing microorganisms; and FIG. 7 is a cross sectional, elevational side view of the test device of FIGS. 1–3, taken along line 6—6 of FIG. 2 and in which the first and second compartments communicate with each other to mix the contamination indicating agent of the second compartment with the nutrient containing liquid of the first compartment.

DETAILED DESCRIPTION OF THE PREFERRED EMBODIMENT

In the appended drawings, the test device in accordance with the present invention is generally identified by the reference 10. Also, the same elements are identified by the same references in the different Figures of these drawings.

As illustrated in FIGS. 1–4, the test device 10 is formed of a three-part hollow container unit formed of a substantially cylindrical tubular section 11, a first end cap section 12 and a second end cap section 13.

The tubular section 11 is preferably molded from transparent plastic material and comprises a color chart 14 (FIG. 1) usable to evaluate the level of microbial contamination of the liquid, as will be more fully described in the following description.

Tubular section 11 further comprises a pair of axially spaced apart legs 15 and 16 for supporting the test device 10 on an horizontal, generally flat surface.

As shown on FIG. 4, the tubular section 11 comprises a first end 17 having a threaded external surface formed with a circular groove 18. An annular sealing member 19, has a J-shaped cross section to snugly fit on the first end 17 of the tubular section 11 as illustrated in FIG. 4. The sealing member 19 comprises an annular tongue 20 snugly fitted into the circular groove 18 to retain the sealing member 19 on the end 17 of the tubular section 11, an outer chamfered edge 21 and an inner chamfered edge 22.

Tubular section 11 also comprises a second end 23 having a threaded external surface formed with a circular groove 24. An annular sealing member 25, has a J-shaped cross section to snugly fit on the second end 23 of the tubular section 11 as illustrated in FIG. 4. The sealing member 25 comprises an annular tongue 26 snugly fitted into the circular groove 24 to retain the sealing member 25 on the end 23 of the tubular section 11, an outer chamfered edge 27 and an inner chamfered edge 28.

Cap section 13 is advantageously made of molded plastic material and is formed with a distal end wall 29 perpendicular to the longitudinal axis 30 of the tubular section 11. Cap section 13 further comprises coaxial inner and outer substantially cylindrical walls 31 and 32 connected to and extending from one side of the distal end wall 29. The outer cylindrical wall 32 has an internal threaded surface engaging the threaded external surface of the end 23 to enable screwing of the cap section 13 on the tubular section 11. The internal surface of the outer cylindrical wall 32 is also formed with a beveled shoulder 33 coaxial with the outer cylindrical wall 32 for abutting against the outer chamfered edge 27 of the sealing member 25 and thereby form a sealed joint. The inner cylindrical wall 31 is formed with an annular beveled free end 34 abutting against the chamfered edge 28 of the sealing member 25 to form a sealed joint.

As illustrated in FIG. 4, the cap section 13 can be screwed on the externally threaded end 23 of the tubular section 11 to press the sealing member 25 between the end 23 and the annular beveled free end 34 and between the beveled shoulder 33 and the end 23 of the tubular section 11, and thereby form a sealed beveled compartment 35. Therefore, a first compartment 36 is defined within the tubular member 11 and is extended by the internal space of the inner cylindrical wall 31, and a second compartment, which is the sealed annular compartment 35, is defined by the empty space between the inner and outer cylindrical walls 31 and 32. FIG. 4 shows the first compartment 36 containing a nutrient 37, for example a lyophilised culture, and the second compartment 35 containing a contamination indicating agent 38, for example a coloring agent.

Still referring to FIG. 4, the first 36 and second 35 compartments are isolated from each other through sealing means comprising the inner cylindrical wall 31 and the annular sealing member 25.

The cap section 12 is advantageously made of molded plastic material. It comprises an annular distal end wall 39 perpendicular to the longitudinal axis 30 of the tubular section 11 and formed with a central circular hole 40 therein. Cap section 12 further comprises an outer substantially cylindrical wall 41 connected to and extending from one side of the distal end wall 39. The outer cylindrical wall 41 has an internal threaded surface engaging the threaded external surface of the end 17 to enable screwing of the cap section 12 on the tubular section 11. The internal surface of the outer cylindrical wall 41 is also formed with a beveled shoulder 42 coaxial with the outer cylindrical wall 41 for abutting against the outer chamfered edge 21 of the sealing member 19 and thereby form a sealed joint.

Cap section 12 further comprises a substantially circular wall 43 coaxial with the distal end wall 39 and with the cylindrical wall 41 but having a diameter smaller than those of the walls 39 and 41. As depicted in FIG. 4, the circular wall 43 is mounted inside the cylindrical wall 41 spaced apart from the distal end wall 39. Spaced apart axial members such as 44 interconnect the contour of the hole 40 in the distal end wall 39 with the periphery of the circular wall 43. This circular wall 43 is formed with a peripheral beveled circular edge 45 abutting against the inner chamfered edge 22 of the sealing member 19 to form a sealed joint.

As illustrated in FIG. 4, the cap section 12 can be screwed on the externally threaded end 17 of the tubular section 11 to press the sealing member 19 between the end 17 of the tubular section 11 and the peripheral beveled circular edge 45 of wall 43, and between the beveled shoulder 42 and the end 17 to thereby seal the first compartment 36.

The test device in accordance with the present invention is intended to be sold in the form shown in FIG. 4. To carry out a microbial contamination test, the following steps are performed.

Although the following procedure relates to a bacterial contamination test made on water from a dental unit, it should be kept in mind that other microbial contamination tests can be performed on other liquids as long as suitable nutrient 37 and contamination indicating agent 38 are employed.

In a first step (FIG. 5), cap section 12 is unscrewed to displace that cap section axially on the tubular section 11 in direction 47 and form an annular passage 46 between the peripheral beveled edge 45 of the circular wall 43 and the inner chamfered edge 22 of the annular sealing member 19. Water 48 for example from a dental syringe 49 is projected through the hole 40 in the wall 39 and penetrates the compartment 36 through the spacing between the axial members 44 and the annular passage 46. During this operation, the sealing member 19 forms an annular sealed joint to prevent passage of water between the end 17 of the tubular section 11 and the internal surface of the outer cylindrical wall 41 of the cap section 12. Also, an axial post 50 (FIG. 4) extends from the circular wall 43 toward the central hole 40 to prevent splashing of the water 48 projected through the hole 40.

After the first compartment 36 has been filled with water, the cap section 12 is screwed to displace that cap section axially on the tubular section 11 in direction 51 (FIG. 6) and press the sealing member 19 between the end 17 of the tubular section 11 and the peripheral beveled circular edge 45 of wall 43, and between the beveled shoulder 42 and the end 17, to thereby seal the first compartment 36. The test device 10 is then shaken to mix (see arrows 52) the lyophilised culture (nutrient) 37 with the water 48. The test device is then placed on the legs 15 and 16 to grow the bacteria of the water during a predetermined period of time. During growth of the bacteria, gaseous exchange is enabled by means of a passage 53 made by grooving the end 17 of the tubular section 11 both internally and externally.

After the predetermined period of time has elapsed, a second step consists of unscrewing the cap section 13 to displace that cap section axially on the tubular section 11 in direction 54 (FIG. 7) and form an annular passage 55 between the annular beveled free end 34 of the inner cylindrical wall 31 and the inner chamfered edge 28 of the annular sealing member 25. The compartments 35 and 36 are then in communication with each other whereby the contamination indicating agent 38 from the second compartment 35 mix with the bacteria containing water from the first compartment 36. The contamination indicating agent 38 then reacts by coloring the water in the presence of bacteria. As the tubular section 11 is transparent, the user can compare the color of the water with the colors of the chart 14 (FIG. 1) to determine the degree of contamination of the liquid. Again the sealing member 25 forms an annular sealed joint between the end 23 of the tubular section 11 and the internal surface of the outer cylindrical wall 32 to thereby prevent escape of water.

Finally, it should be pointed out that a multitude of microbial contamination tests can be carried out with the device according to the invention provided that appropriate nutrient 37 and contamination indicating agent 38 are selected for each particular test.

Although the present invention has been described hereinabove by way of a preferred embodiment thereof, this embodiment can be modified at will, within the scope of the appended claims, without departing from the spirit and nature of the present invention.

What is claimed is:

1. A test device for evaluating microbial contamination of a liquid, comprising:

a hollow container unit including a tubular section having one end and a cap section mounted on said one end of the tubular section, said tubular section defining a first compartment for containing a nutrient for growing microorganisms and said cap section defining a second compartment for containing a contamination indicating agent;

inlet means for introducing said liquid into the first compartment whereby said liquid mixes with said nutrient to grow microorganisms present in said liquid; and sealing means interposed between the first and second compartments and operable (a) to isolate the first and second compartments from each other, or (b) to establish communication between said first and second compartments to mix said agent from the second compartment with said liquid from the first compartment and enable said agent to indicate, in the presence of microorganisms, contamination of the liquid; wherein:

(a) said cap section is formed with a distal end wall and with coaxial inner and outer tubular walls connected to and extending from one side of said distal end wall, said second compartment being defined between said inner and outer tubular walls;

(b) said inner tubular wall of the cap section comprises an annular free end;

(c) said sealing means comprise said inner tubular wall and an annular sealing member interposed between said annular free end and said one end of the tubular section; and (d) said test device further comprises means for displacing said cap section axially on said one end of the tubular section between a first position in which the annular sealing member is pressed between said annular free end and said one end of the tubular member to isolate said first and second compartments from each other, and a second position in which an annular passage is formed between said annular free end and said one end of the tubular section whereby said first and second compartments are in communication with each other.

2. The test device of claim 1, in which said cap section displacing means comprises:

said one end of the tubular section being substantially cylindrical and externally threaded;

said outer tubular wall of the cap section being substantially cylindrical and internally threaded to engage the externally threaded end of the tubular section and enable screwing of said cap section on said tubular section; and whereby, in operation, said cap section is screwed on said externally threaded end of the tubular section to press said annular sealing member between said annular free end and said externally threaded end and thereby isolate said first and second compartments from each other, and unscrewed to form the annular passage between said annular free end and said externally threaded end whereby said first and second compartments are in communication with each other.

3. The test device of claim 1, wherein said outer tubular wall comprises an inner surface formed with an annular shoulder coaxial with said outer tubular wall, wherein upon displacing said cap section axially on said one end of the tubular section toward said first position, said annular sealing member is pressed between said annular shoulder and said one end of the tubular section for the purpose of sealing the second compartment.

4. The test device of claim 1, in which said inner tubular wall defines an inner cavity that extends the first compartment.

5. The test device of claim 1, in which said annular sealing member is mounted on said one end of the tubular member.

6. A test device for evaluating microbial contamination of a liquid, comprising:

a hollow container unit defining a first compartment for containing a nutrient for growing microorganisms and a second compartment for containing a contamination indicating agent, said hollow container unit comprising a tubular section having one end and a cap section mounted on said one end of the tubular section, said tubular section defining said first compartment;

inlet means for introducing said liquid in the first compartment whereby said liquid mixes with said nutrient to grow microorganisms present in said liquid; and sealing means interposed between the first and second compartments and operable (a) to isolate the first and second compartments from each other, or (b) to establish communication between said first and second compartments to mix said agent from the second compartment with said liquid from the first compartment and enable said agent to indicate, in the presence of microorganisms, contamination of the liquid;

wherein said cap section is formed with:

a distal end wall formed with a central hole therein;

a tubular wall connected to and extending from one side of the distal end wall;

a substantially circular wall coaxial with said tubular wall, having a diameter smaller than the diameter of said tubular wall, mounted inside said tubular wall, and spaced apart from said distal end wall; and means for connecting the circular wall to said distal end wall while leaving a passage between the contour of the central hole of the distal end wall and the periphery of the circular wall through which said liquid is introduced into the first compartment; and said test device further comprises an annular sealing member interposed between the periphery of said circular wall and said one end of the tubular section, and means for displacing said cap section axially on said one end of the tubular section between a first position in which the annular sealing member is pressed between said circular wall and said one end of the tubular section for the purpose of closing and sealing said first compartment, and a second position in which an annular passage is formed between the periphery of said circular wall and said one end of the tubular member to enable liquid to be introduced into the first compartment through said passages.

7. The test device of claim 6, wherein said cap section displacing means comprises:

said one end of the tubular section being substantially cylindrical and externally threaded;

said tubular wall being generally cylindrical and internally threaded to engage said externally threaded end of the tubular section; and whereby, in operation, said cap section is screwed on said externally threaded end of the tubular section to press said annular sealing member between said circular wall and said externally threaded end for the purpose of closing and sealing said first compartment, and unscrewed to form the annular passage between the periphery of said circular wall and said externally threaded end to enable liquid to be introduced into the first compartment through said passages.

8. The test device of claim 6, in which said circular wall is provided with a generally central post extending toward the central hole in the distal end wall in order to prevent splashing of liquid projected through said hole when introducing liquid into said first compartment.

9. The test device of claim 6, in which said one end of the tubular member is grooved internally and externally to form a channel providing for gaseous exchange between the inside of the first compartment and the outside of said test device.

* * * * *

UNITED STATES PATENT AND TRADEMARK OFFICE
CERTIFICATE OF CORRECTION

PATENT NO. : 5,455,176

DATED : 3 October 1995

INVENTOR(S) : André Prevost, et al.

It is certified that error appears in the above-identified patent and that said Letters Patent is hereby corrected as shown below:

In column 3, line 63, "beveled" should be --annular--.

In column 7 (claim 6), line 31, "member" should be --section--.

In column 7 (claim 6), line 32, "passages" should be --passage--.

Signed and Sealed this

Thirtieth Day of April, 1996

Attest:

BRUCE LEHMAN

*Attesting Officer*  *Commissioner of Patents and Trademarks*